US00PP31340P2

(12) United States Plant Patent
Miller

(10) Patent No.: US PP31,340 P2
(45) Date of Patent: Jan. 7, 2020

(54) ***AGAPANTHUS* PLANT NAMED 'MBNAGVAR18'**

(50) Latin Name: ***Agapanthus* hybrid**
Varietal Denomination: MBNAGVAR18

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 0 days.

(21) Appl. No.: 15/932,992

(22) Filed: Jun. 5, 2018

(51) Int. Cl.
*A01H 5/02* (2018.01)
*A01H 6/04* (2018.01)

(52) U.S. Cl.
USPC ..... Plt./398
CPC ..... *A01H 6/04* (2018.05)

(58) Field of Classification Search
USPC ..... Plt./398
CPC ..... A01H 6/56; A01H 5/02; A01H 6/04
See application file for complete search history.

*Primary Examiner* — Kent L Bell
(74) *Attorney, Agent, or Firm* — Cassandra Bright

(57) ABSTRACT

A new and distinct *Agapanthus* cultivar named 'MBNAGVAR18' is disclosed, characterized by reliable flowering, variegated leaves and small growth form. The new variety is tolerant of glyphosate and sterile. The new variety is a *Agapanthus*, typically produced as an outdoor ornamental plant.

2 Drawing Sheets

Figure 1:
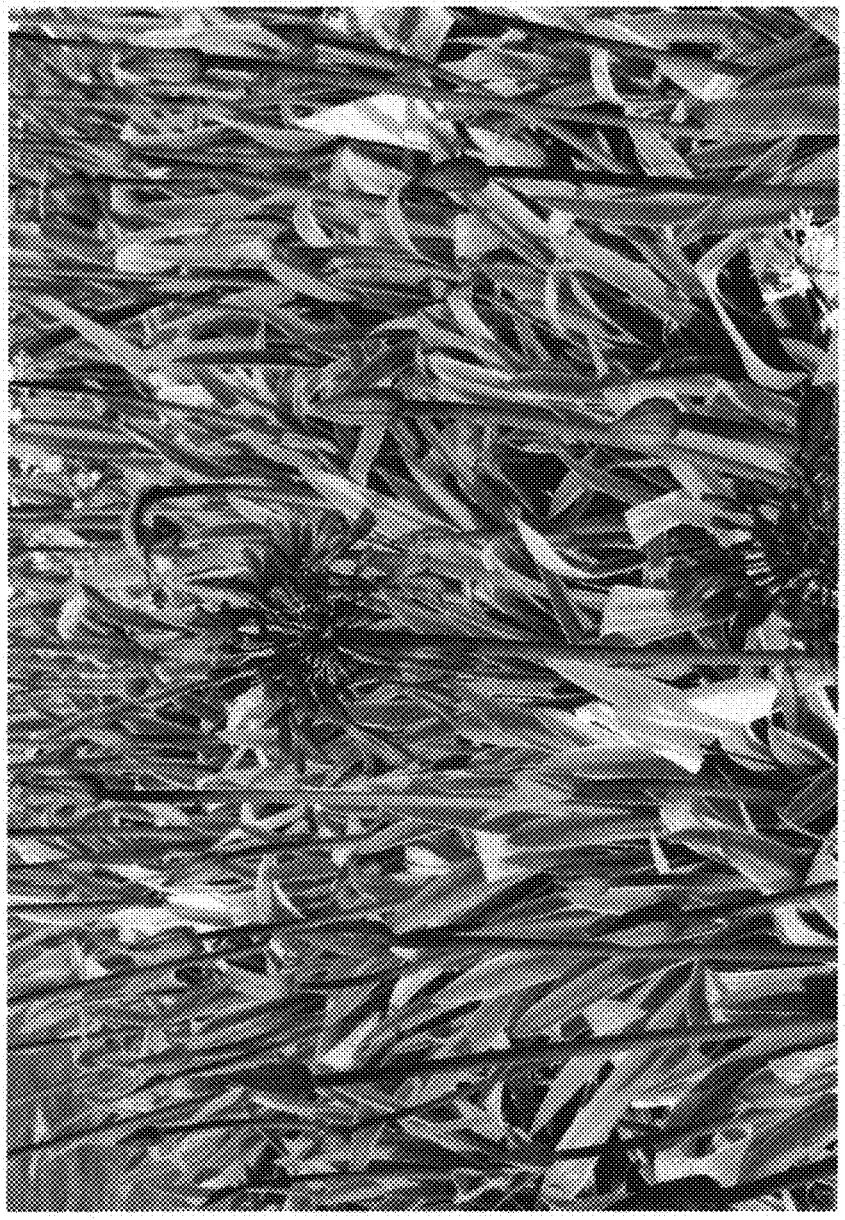

Latin name of the genus and species: *Agapanthus* hybrid.
Variety denomination: 'MBNAGVAR18'.

BACKGROUND OF THE INVENTION

The new cultivar is the product of chance discovery. The new variety originated as a naturally occurring whole plant mutation of the unpatented 'Storm Cloud' variety of *Agapanthus*.

The new variety was first observed by the inventor, Luen Miller, during July 2003, in Royal Oaks, Calif., and was selected in. the Fall of 2004.

Subsequent asexual reproduction of the new cultivar 'MBNAGVAR18' was first performed by division in Royal Oaks, Calif., during Fall of 2004. Access to all plants was restricted, as plants were kept in a location not open to the public. Through subsequent propagation, multiple generations have been reproduced, which have shown that the unique features of this cultivar are stable and reproduced true to type.

SUMMARY OF THE INVENTION

The cultivar 'MBNAGVAR18' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MBNAGVAR18'. These characteristics in combination distinguish 'MBNAGVAR18' as a new and distinct *Agapanthus* cultivar:

1. Variegated foliage.
2. Good bloom vigor.
3. Minimal loss of flower color intensity.

4. Good growth vigor.
5. Dark purple-blue flowers.

PARENT COMPARISON

Plants of the new cultivar 'MBNAGVAR18' are similar to the parent, *Agapanthus* 'Storm Cloud' in most horticultural characteristics. The new variety, however, differs in the following ways:

1. The new variety produces variegated foliage, compared to the solid colored foliage of parent 'Storm Cloud'.
2. Flowers of 'MBNAGVAR18' have a slightly different shade of purple-blue than those of parent 'Storm Cloud',
3. The new variety has a slightly less vigorous growth habit than that of 'Storm Cloud'.

COMMERCIAL COMPARISON

Plants of the new cultivar 'MBNAGVAR18' are similar to the commercial variety *Agapanthus* 'DunAga02', U.S. Plant Pat. No. 25,957 in most horticultural characteristics. The new variety, however, differs in the following:

1. 'MBNAGVAR18' produces much deeper purple-blue flowers than those of 'DunAga02'.
2. 'MBNAGVAR18' has thinner variegation stripes across the central portion of the blade than 'DunAga02'.
3. Plants of the new variety produce longer scapes than 'DunAga02'.
4. Foliage margin is less broadly variegated than 'DunAga02'.

Plants of the new cultivar 'MBNAGVAR18' are similar to the commercial variety *Agapanthus* 'Goldstrike', U.S. Plant Pat. No. 20,650, in most horticultural characteristics. The new variety, however, differs in the following:

1. 'MBNAGVAR18' has a much deeper flower color than 'Goldstrike'.
2. 'MBNAGVAR18' has longer scapes than 'Goldstrike'.

3. The new variety initiates and develops more flower spikes than 'Goldstrike'.
4. New variety is a larger plant than 'Goldstrike'.
5. Variegation of 'MBNAGVAR18' is more creamy yellow, compared to the more intense yellow of 'Goldstrike'.

BRIEF DESCRIPTION OF THE PHOTOGRAPHS

The accompanying photograph in FIG. 1 illustrates in full color a typical foliage of a 1.5-year-old 'MBNAGVAR18' grown in Royal Oakes, Calif.

Figure 2:
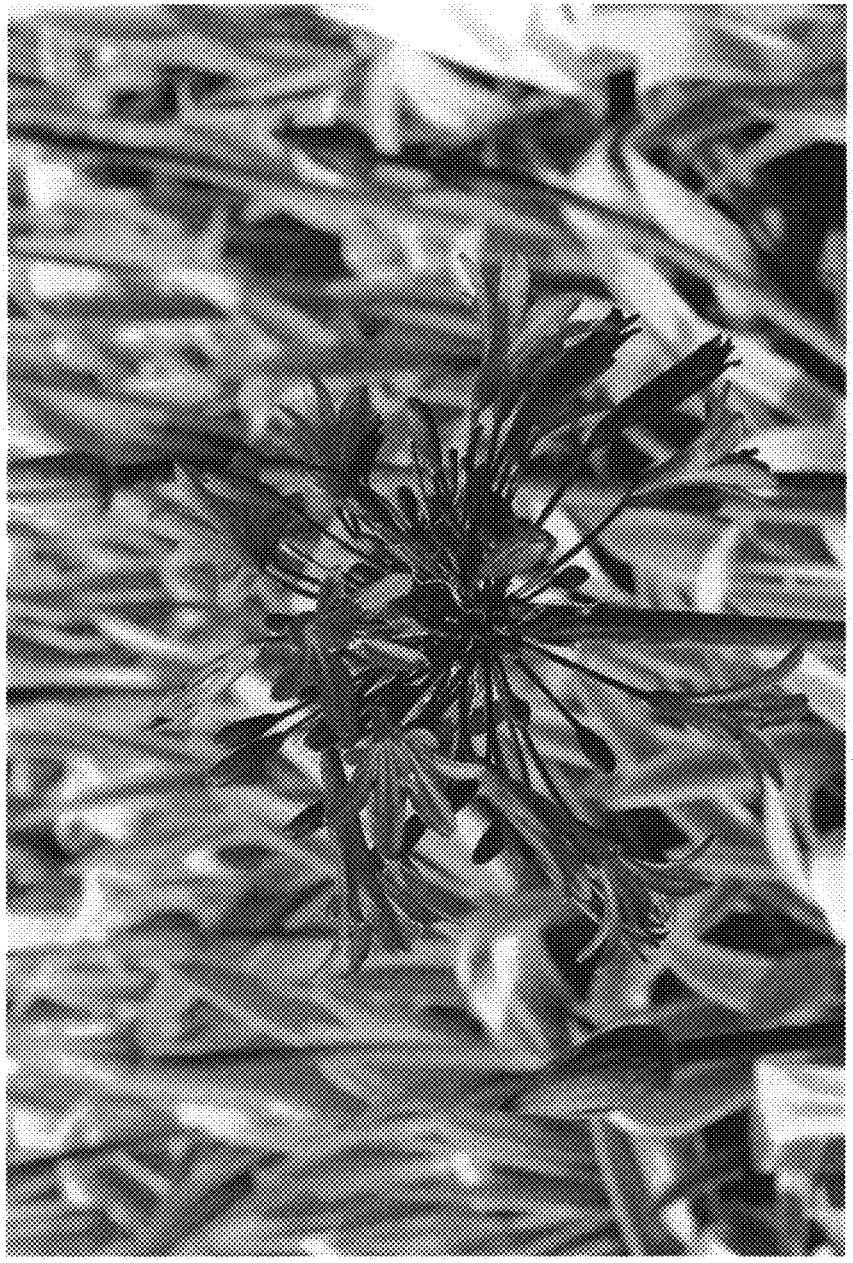

FIG. 2 illustrates in full color a close up of the flowers of a 1.5-year-old 'MBNAGVAR18'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'MBNAGVAR18' plants grown outdoors in Royal Oaks, Calif. Plants are approximately 1 year old. Temperatures ranged from approximately 8° C. to 15° C. at night and 10° C. to 32° C. during the day. No artificial light, photoperiodic treatments were given to the plants. No chemical treatments were given to plants. Measurements and numerical values represent averages of typical plant types.

Botanical classification: *Agapanthus hybrida* 'MBNAGVAR18'.

PROPAGATION

Root description: Thick, fleshy root system colored near Brown 199D and Orange-White 159C.

PLANT

Growth habit: Clump forming tender perennial with arching, pendulous foliage. Plants evergreen to −5° F.

Height: Foliar plane 40 to 50 cm. Flowering plane 70 to 80 cm.

Plant spread: Approximately 60 cm.

Growth rate: Moderate, slower growth than non-variegated forms.

Diameter of stem: Flower stems 5 to 8 mm.

Growth pattern: The plant makes growth throughout most of the year but particularly in the summer months. This grow is in the form of basal shoots or pups as well as some leaf extension. From mid-summer flowers start to appear and remain for much of the summer.

FOLIAGE

Leaf:

*Average leaf length*.—Approximately 20 to 25 cm

*Average leaf width*.—Approximately 1.0 to 1.8 cm.

*Arrangement*.—Basal, irregular whorls.

*Shape of blade*.—Linear.

*Apex*.—Acute.

*Margin*.—Entire.

*Texture of top surface*.—Smooth.

*Texture of bottom surface*.—Smooth.

*Quantity of leaves per plant*.—Average 30 to 40.

*Color*.—Mature Upper surface: Center of blade near Green 137C, streaks near Yellow 2D, margin near Yellow 11C. Mature Lower surface: Center of blade near Green 138A and 138B, colors present individually, mostly striped. Green center streaked with Yellow 4C. Margin near Yellow 8C. Immature Upper surface: Striped Green 137B and Yellow-Green 154B. Immature Lower surface: Striped Green 137B and Yellow-Green 154B.

*Base*.—Truncate, non-clasping.

*Aspect*.—First year growth is mainly upright, slightly upwardly curved. With maturity foliage becomes more arched.

FLOWER

Natural flowering season: Begins flowering in May, in California.

Length of flowering period: Approximately 8 weeks.

Inflorescence type: Terminal Umbel with approximately 20 individual flowers and 5 to 10 buds.

Individual flower type: Single.

Flower profile: Funnelform.

Lasting quality: Inflorescence shows no significant signs of aging for approximately 5 to 6 weeks.

Bud:

*Shape*.—Narrow ovate.

*Length*.—Approximately 2.1 cm.

*Diameter*.—Approximately 0.7 cm.

*Color*.—Near RHS Violet-Blue 91A, apex near 93B.

Umbel size:

*Diameter*.—Average 13 cm.

*Height*.—Average 7 cm.

Corolla:

*Arrangement*.—Apetalous, single, campanulate flowers composed of 6 basally fused tepals, shaped into a flared trumpet.

*Size*.—Length: Approximately 3.0 cm. Width: Approximately 3.3 cm at widest point. Lobe Length: Approximately 1.8 cm. Lobe Width: Average range 0.7 cm.

*Margin*.—Entire.

*Shape*.—Lanceolate.

*Apex*.—Broadly acute.

*Texture*.—Glabrous all surfaces.

Color:

*Tepals*.—When opening: Outer surface: Near Violet-Blue 93B, streaked 93A. Inner surface: Near Violet-Blue 93C, streaked 93B. Fully opened: Outer surface: Near Violet-Blue 93C, streaked 93B. Inner surface: Near Violet-Blue 93D, streaked 93B. Color Changes when Aging: Outer surface: Near RHS Violet-Blue 93B. Inner surface: Near RHS Violet-Blue 93D.

*Sepals*.—Not Present.

Fragrance: Moderately strong musty scent.

*Perianth tube*.—Length: 0.8 cm. Color: Inner surface: Near Violet-Blue 92D. Outer surface: Near Violet-Blue 93B.

Flower filament color: Upper section near Violet-Blue 90D, lower section near 91D.

Flower anther color: Near Violet-Blue 90A.

Anther quantity: 6, each approximately 0.2 cm long.
Stamen protrusion: Not protruding past the floral lobe apex.
Pistil:
*Number.*—1.
*Length.*—Approximately 1.5 cm.
*Stigma.*—Shape: Linear. Color: Near Violet-Blue 91D.
Pollen: Not observed.
Flower style color: Near Violet-Blue 90C.
Pedicel:
*Length.*—1.8 to 2.5 cm.
*Texture.*—Glabrous.
*Color.*—Near Green 137A, heavily flushed Greyed-Purple N187A.
Peduncle:
*Length.*—Average range 55 to 65 cm.
*Diameter.*—1.5 to 2.0 cm
*Texture.*—Glabrous.
*Color.*—Near Green 138B, heavily flushed Greyed-Purple N187C, closer to flower head flushed near N187B.
Fragrance: None.

OTHER CHARACTERISTICS

Seed production: Sterile, no seed produced to date.
Disease resistance: Seems unaffected by any disease.
Temperature tolerance: Not tested but expected to handle −5° C. to +30° C.
Drought tolerance: Will tolerate considerable dryness once established.

What is claimed is:

1. A new and distinct cultivar of *Agapanthus* plant named 'MBNAGVAR18' as herein illustrated and described.

* * * * *